United States Patent
Martin et al.

[11] 4,158,134
[45] Jun. 12, 1979

[54] METHOD AND APPARATUS FOR AUTOMATICALLY RECOGNIZING FAULTS IN THE SURFACE OF THE DIMENSIONS OF AN OBJECT

[75] Inventors: Rolf Martin, Planegg; Norbert Roth; Ruediger Froese-Peeck, both of Munich, all of Fed. Rep. of Germany

[73] Assignee: Siemens Aktiengesellschaft, Berlin & Munich, Fed. Rep. of Germany

[21] Appl. No.: 870,850

[22] Filed: Jan. 19, 1978

[30] Foreign Application Priority Data

Feb. 20, 1977 [DE] Fed. Rep. of Germany ....... 2704983

[51] Int. Cl.$^2$ ............................................. H01J 3/14
[52] U.S. Cl. ................................ 250/216; 250/578; 350/181
[58] Field of Search ............... 350/181, 190; 358/212, 358/213; 250/216, 578, 211 J; 356/156, 157, 162

[56] References Cited

U.S. PATENT DOCUMENTS

| 3,475,614 | 10/1969 | Bullard | 350/181 |
| 4,053,773 | 10/1977 | Deresh et al. | 250/578 |

*Primary Examiner*—David C. Nelms
*Attorney, Agent, or Firm*—Hill, Van Santen, Steadman, Chiara & Simpson

[57] ABSTRACT

A method and apparatus is disclosed for the automatic and rapid recognition of faults in a surface or dimensions of an object, or for recognizing a position of the object in a field of view of an observation and/or measuring device. A photodiode row is provided having an active surface with a length dimension substantially greater than its width dimension. An anamorphotic lens system is provided which focuses a first dimension of the field of view onto the active surface length dimension and which focuses a second orthogonal dimension of the field of view onto the active surface width dimension. By means of signals from the photodiode row, theoretical dimensions can be compared with actual measured dimensions of the object.

5 Claims, 6 Drawing Figures

METHOD AND APPARATUS FOR AUTOMATICALLY RECOGNIZING FAULTS IN THE SURFACE OF THE DIMENSIONS OF AN OBJECT

BACKGROUND OF THE INVENTION

The invention relates to a process and a device for the automatic and rapid recognition of faults in the surface or the dimensions of an object, and also for recognizing the position of the object in the field of view or field of operation of a measuring or operating device, employing a focusing optics and a row of photo-diodes.

For the automatic recognition of faults in an object, it is known to focus the area of the object which is to be investigated onto a projector provided with a scale employing an anamorphotic lens system. In this way a comparatively small fault occurring only in one coordinate direction can be clearly recognized and measured. The linear dimensions of an object are determined, as is known, using so-called rows of photodiodes. The section of the object which is to be measured is focused onto the diode row employing a lens system; if, on the other hand, the surface of an object arranged, for example, in the field of view of a measuring device is to be investigated or measured, a photodiode matrix is employed. The individual diodes of the matrix can be operated by means of a shift register. They are consecutively connected to a data signal integrator with the frequency of a pulse generator. Thus it is possible to determine the dimensions of the object taking into account the focusing factor. Furthermore, by means of an actual-theoretical value comparison of the measured voltage signals with stored values, it is possible to recognize structure faults or a fault relative to the position of the object within the field of view of a measuring device or in the operating field of an operating device. A measuring device of this type which operates by means of a photodiode matrix or a photodiode row is known per se. The expense required to drive and analyze the quantity of data supplied by a photodiode matrix is comparatively high in comparison to a photodiode row which contains a considerably smaller number of photodiodes. This constitutes a disadvantage if, for example, the objects in question (small work pieces) are to be investigated. Often, for example, it is only necessary to determine whether the object lying in the field of view is damaged and must thus be eliminated from a series. The question as to where the damage is situated and the nature of the damage is here of subordinate importance. In processing machines it must frequently be insured that the object is arranged correctly in the feeder to the operating station or is positioned within the operating field of the machine. With high-speed machines, the times available are short since a recognized fault necessitates further treatment.

SUMMARY OF THE INVENTION

An object of the invention is, for the automatic recognition of faults in the surface or the dimensions of an object or for the recognition of the position of the object in the field of view of an observation and/or measuring device employing a photodiode row and a focusing optics, to reduce the detection and analysis times in such manner that moving objects can also be investigated. In accordance with the process of the invention, an anamorphotic lens system is used to construct the surface of the field of view in one of the main coordinate directions, and the entire surface of the field of view is focused onto the active surface of a photodiode row in the other main coordinate direction. With this procedure, only one diode row is sufficient, whereby the access times and analysis times, and also the expense for electronics is considerably reduced. As previously described, the entire field of view is focused onto the active surface of the diode row. The video-signal formed from the sequence of individual signals has a particular course, in particular with simple geometric structures. Edges in the surface image produce jumps in the signal level. With a sufficient resolution in a quantity of data which, although small, is made available relatively rapidly, the video-signal supplied by the diode row contains sufficient information regarding the position and/or properties of the object. It goes without saying that this procedure does not satisfy the requirements in every case, such as when the desired fault quantity which is to be recognized lies in the region of or even below the signal level fault tolerance governing each active diode surface of the row.

First a device is provided for the automatic measurement of length and/or the position of an object to be measured in the field of view, consisting of a focusing optics for projecting at least one length dimension of the object to be measured onto a photodiode row. A device which serves to implement the process of the invention consists of an anamorphotic lens arrangement for the focusing optics comprising two cylinder axes which are orthogonal to one another. One of the anamorphotic lenses transmits the field of view of the measuring device onto the length dimension of the active surface of the diode row, and the other anamorphotic lens contracts the width of the field of view onto the width dimension of the active surface of the diode row. Thus, in each case an object lying in the field of view is likewise focused on the photodiode row. For several functions which occur in practice, the facilities for the recognition of marked faults are adequate when only one photo-diode row is used.

DESCRIPTION OF THE PREFERRED EMBODIMENTS

Figure 1:
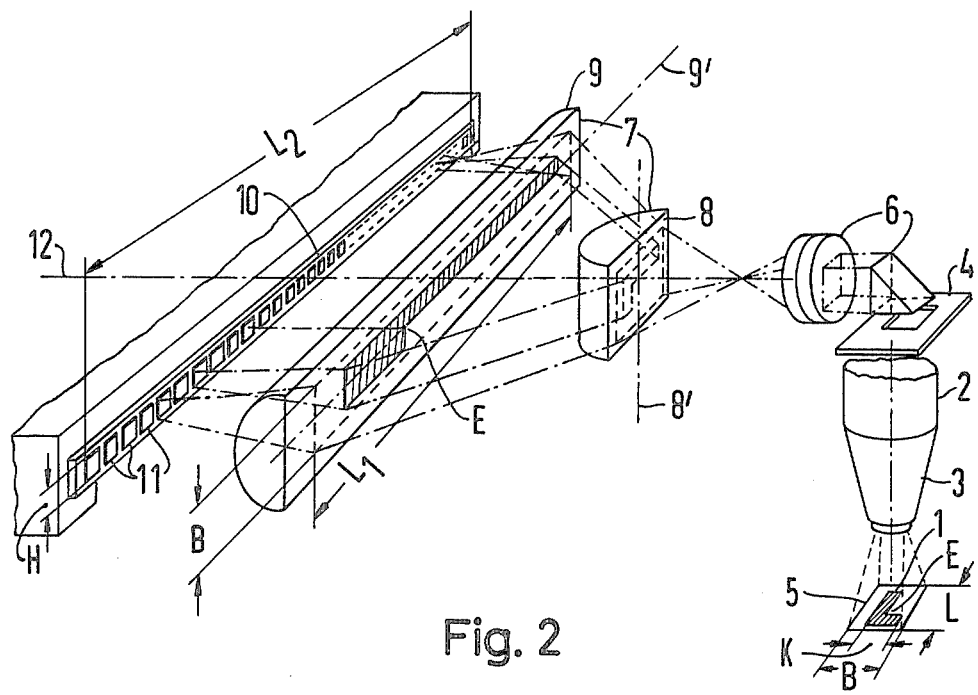
FIG. 1 is a diagrammatic illustration of the invention for explaining the process of the invention.

In the processing field of a processing machine which has not been shown here, there is arranged a work piece which is to be processed and the size of which is on the order of e.g. 2×2 mm, namely the object 1. A measuring device-generally referenced 2-possesses an objective 3 with a field stop 4 arranged therein. It delimits the field of view 5 in which the object 1 is arranged. The width of the field of view here is referenced B and the length L. In the present example the field of view 5 is projected-here by means of an inverted image optics 6-onto an anamorphotic lens system 7 consisting of the cylinder lenses 8 and 9. The optical axes 8' and 9' of the cylinder lenses are orientated at right angles to one another. In place of the cylinder lenses which have been shown here in simplified form and which are arranged at a distance from one another, a layered lens system is used. The cylinder lenses arranged in this way relative to one another operate as a double anamorphotic system. A diode row 10 is arranged axially parallel to the axis 9' of the cylinder lens 9. The photo-diode row bears the individual photodiodes 11 arranged next to one another. By means of the cylinder lens 8, the field of view 5 is projected onto the cylinder lens 9. The length L of the field of view 5 here is stretched to the length $L_1$. This length $L_1$ is somewhat shorter than the length $L_2$ of the active surface F of the photo-diode row 10. On the other hand, the cylinder lens 9 contracts the width B of the field of view 5 to the width $B_1$. Width $B_1$ is somewhat smaller than the width H of the active surface of the diode row. If the entire anamorphotic system 7 with the diode row 10 is rotated about the optical axis 12, a change occurs in the focusing conditions with respect to the dimensions B and L of the field of view 5.

Figure 2:
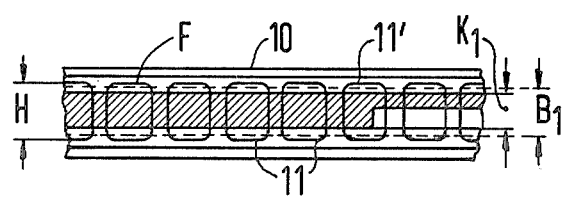
FIG. 2 is a section of a photo-diode row corresponding to FIG. 1.

FIG. 2 is a section through the object image projected by the cylinder lens 9, in accordance with FIG. 1, onto the diode row 10. As can be seen, here the width K of the object lying in the field of view 5 is constricted to the value $K_1$. Due to the fact that the entire width B of the image, contracted by the anamorphotic lens system to the width $B_1$, lies within the height of the field of the photodiode row F, the individual photodiodes 11 are exposed to different light intensities. The corner edge E of the object 1 here is focused, for example, on the photodiode 11' of the photodiode row 10. During the read-out of the photodiode row, the different light intensities produce voltage signals of different levels. The analysis logic and the actual-theoretical value comparison by means of an analysis logic are known and do not constitute the subject of the invention.

Figure 3:
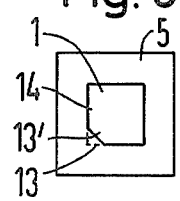
FIG. 3 illustrates an object having a faulty contour arranged in a field of view of a processing device.

FIG. 3 illustrates an object 1 arranged in the field of view 5, having a corner 13 which is faulty, e.g. broken. A spot 14 is also present on the surface of the object, indicating a pollution of the surface of the object.

Figure 4:
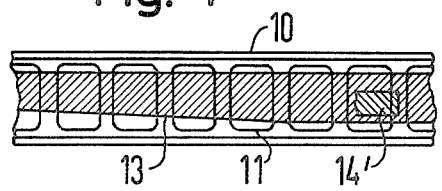
FIG. 4 is a section of a diode row in accordance with FIG. 1 with an object corresponding to FIG. 3 projected thereupon.

As shown in FIG. 4, the broken edge 13' of the object 1 would be represented by a voltage signal, differing from the standard level, of the individual photo-diodes 11. Correspondingly the spot 14 represented on the diode row 10 at 14' would lead to a voltage signal deviating from the standard level.

Figure 5:
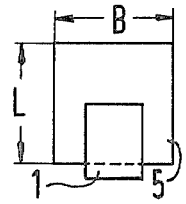
FIG. 5 illustrates an object incorrectly arranged in the field of view of a processing device.

FIG. 5 illustrates an object 1 currently arranged outside of the field of view 5.

Figure 6:
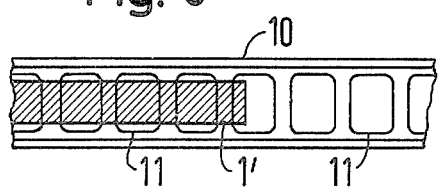
FIG. 6 illustrates the focusing of this object on a photodiode row corresponding to FIG. 1.

FIG. 6 illustrates the object 1', which, in accordance with FIG. 5, has been only partially focused on the diode row. The incorrect position of the object in the field of view 5 results in a pulse sequence deviating from the theoretical value occurring at the output of the shift register which serves to interrogate the individual voltage states of the photo-diodes.

In accordance with the embodiment shown in FIG. 1, in order to achieve a higher recognition capacity it can be advisable to additionally employ a similar, second anamorphotic lens system which, however, is rotated by 90° with respect to the two coordinates, together with analysis logic. This results in a high resolution in the two main coordinate directions of the object, and the detection time and analysis time are considerably shorter in comparison to a diode matrix. Thus it is possible to effect a rapid quality check on the object even in the case of objects moving beneath the objective 3.

Although various minor modifications may be suggested by those versed in the art, it should be understood that we wish to embody within the scope of the patent warranted hereon, all such embodiments as reasonably and properly come within the scope of our contribution to the art.

We claim as our invention:

1. A process for the automatic and rapid recognition of faults in a surface or dimensions of an object, and for the recognition of a position of the object in a field of view of an observation and measuring device by comparing theoretical and actual values of respective stored and measured signals, comprising the steps of: providing a photodiode row; providing a focusing optics with an anamorphotic lens system; constricting a surface of the field of view in one of its main coordinate directions; and in another main coordinate direction focusing an entire surface of the field of view onto an active surface of said photodiode row.

2. An apparatus for automatic measurement of length or position of an object to be measured in a field of view of a measuring device, comprising: a photodiode row; a focusing optics means for projecting at least one length dimension of the object to be measured onto said photodiode row; said focusing optics means having first and second anamorphotic lens means with first and second respective cylinder axes which are orthogonal to one another, said first anamorphotic lens means transferring the field of view of the measuring device to a length of an active surface of said photodiode row and the second anamorphotic lens means contracting a width of the field of view to a width of said active surface of the photodiode row.

3. A process for the automatic and rapid recognition of faults in a surface or dimensions of an object and for recognition of a position of the object in a field of view, comprising the steps of: providing a photodiode row having an active surface with a length substantially greater than its width; providing a focusing optics with an anamorphotic lens system; projecting and focusing a first dimension of the field of view onto said length of the active surface of the photodiode row; projecting and focusing a second dimension of the field of view onto said width of the active surface of the photodiode row; and analyzing the object by measuring output signals of the photodiode row.

4. An apparatus for automatic measurement of dimensions, position, or faults of an object to be analyzed in a field of view, comprising: a photodiode row having an active surface with a length dimension and a substantially smaller width dimension; and an anamorphotic lens system means for focusing a first dimension of the field of view onto said active surface length dimension and for focusing a second orthogonal dimension of the field of view onto said active surface width dimension.

5. The apparatus of claim 4 in which said anamorphotic lens system means comprises a first anamorphotic lens for expanding the field of view first dimension and a second anamorphotic lens for constructing the field of view second dimension.

* * * * *